(12) United States Patent
McDermott et al.

(10) Patent No.: US 9,314,626 B2
(45) Date of Patent: Apr. 19, 2016

(54) VISUAL PROSTHESIS APPARATUS

(71) Applicant: The Bionics Institute of Australia, East Melbourne (AU)

(72) Inventors: Hugh Joseph McDermott, Mt Macedon (AU); Peter John Blamey, South Yarra (AU); Nicholas Campbell Sinclair, Surrey Hills (AU); Kyle Damon Slater, Brunswick West (AU)

(73) Assignee: The Bionics Institute of Australia (AU)

( * ) Notice: Subject to any disclaimer, the term of this patent is extended or adjusted under 35 U.S.C. 154(b) by 122 days.

(21) Appl. No.: 14/350,033

(22) PCT Filed: Oct. 4, 2012

(86) PCT No.: PCT/AU2012/001206
§ 371 (c)(1),
(2) Date: Apr. 4, 2014

(87) PCT Pub. No.: WO2013/049890
PCT Pub. Date: Apr. 11, 2013

(65) Prior Publication Data
US 2014/0236260 A1    Aug. 21, 2014

Related U.S. Application Data

(60) Provisional application No. 61/544,059, filed on Oct. 6, 2011.

(30) Foreign Application Priority Data

Oct. 27, 2011    (AU) ................................ 2011904479

(51) Int. Cl.
*A61N 1/00*    (2006.01)
*A61N 1/36*    (2006.01)

(52) U.S. Cl.
CPC .................................. *A61N 1/36046* (2013.01)

(58) Field of Classification Search
USPC .......................................................... 607/54
See application file for complete search history.

(56) References Cited

U.S. PATENT DOCUMENTS

2004/0102843 A1    5/2004    Yagi
2005/0273141 A1    12/2005   Greenberg et al.
(Continued)

FOREIGN PATENT DOCUMENTS

JP    2006-068404    3/2006
WO   WO-2005/026786   3/2005

OTHER PUBLICATIONS

"International Application No. PCT/AU2012/001206, International Search Report mailed Nov. 14, 2012", 7 pgs.
(Continued)

*Primary Examiner* — Nicole F Lavert
(74) *Attorney, Agent, or Firm* — Schwegman, Lundberg & Woessner, P.A.

(57) ABSTRACT

Visual prosthesis apparatus includes an image receiver, a processor coupled to the image receiver, a stimulation device coupled to the processor, and an eye monitoring device coupled to the processor. The image receiver receives a sequence of images and the processor produces a stimulation signal at least partially in accordance with the received images. The stimulation device receives the stimulation signal and stimulates visual neurons of a user accordingly to provide the user with a visual percept. The eye monitoring device monitors one or more ocular parameters at an eye region of the user, wherein one or more control functions are associated with the monitored ocular parameters. The processor controls the visual prosthesis apparatus in accordance with the monitored ocular parameters and the associated control functions. The one or more ocular parameters can include pupil size, state of closure of the user's eyelid and direction of eye gaze.

27 Claims, 4 Drawing Sheets

(56) References Cited

U.S. PATENT DOCUMENTS

| | | |
|---|---|---|
| 2008/0046033 A1 | 2/2008 | McClure et al. |
| 2008/0077196 A1* | 3/2008 | Greenberg ........... A61N 1/0543 607/54 |
| 2010/0036457 A1 | 2/2010 | Sarpeshkar et al. |

OTHER PUBLICATIONS

"International Application No. PCT/AU2012/001206, International Written Opinion mailed Nov. 14, 2012", 6 pgs.

* cited by examiner

VISUAL PROSTHESIS APPARATUS

PRIORITY CLAIM TO RELATED APPLICATIONS

This application is a national stage application under 35 U.S.C. §371 of PCT/AU2012/001206, filed Oct. 4, 2012, and published as WO 2013/049890 on Apr. 11, 2013, which claims priority to U.S. Provisional Application No. 61/544,059, filed Oct. 6, 2011, and which claims priority to Australia Application No. 2011904479, filed Oct. 27, 2011, which applications and publication are incorporated by reference as if reproduced herein and made a part hereof in their entirety, and the benefit of priority of each of which is claimed herein.

FIELD

The subject matter disclosed herein relates to apparatus for stimulating visual neurons of a user to provide a visual percept to the user's brain.

BACKGROUND

Visual prostheses have been developed to provide a visual percept to blind or partially blind patients. A visual prosthesis commonly includes an implantable component having an electrode array for placement in the eye on or near retinal nerve cells or alternatively, the electrodes may be placed directly on the visual cortex of the brain. Electrical signals are transmitted via the electrodes to the retinal nerve cells or visual cells in the brain, triggering a perception of vision within the patient's brain. The prosthesis can therefore restore or improve vision perception to users whose retinal photoreceptors have become dysfunctional, for example.

Commonly, a visual prosthesis is used in conjunction with an image receiver such as a video camera. A sequence of images detected by the camera is converted into digital image signals by an image processor and transmitted in 'real time' to a processor that processes the image signals. The processor is connected to the electrode array via a plurality of conductors and stimulates nerve cells by means of the electrodes to create a perception of the images.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

In a first aspect, there is provided visual prosthesis apparatus comprising:
an image receiver configured to receive a sequence of images;
a processor coupled to the image receiver, the processor configured to produce a stimulation signal in accordance with the received images;
a stimulation device coupled to the processor, the stimulation device configured to receive the stimulation signal and stimulate visual neurons of a user in accordance with the stimulation signal to provide the user with a visual percept;
an eye monitoring device coupled to the processor such as to monitor one or more ocular parameters of at least one eye region of the user;
wherein one or more control functions are associated with the monitored ocular parameters, and
wherein the processor is configured to control the visual prosthesis apparatus in accordance with the monitored ocular parameters and the associated control functions.

The processor may be configured to adjust the stimulation signal in accordance with the monitored ocular parameters and the associated control functions, for example. Through adjusting the stimulation signal, the processor may vary the visual percept experienced by the user in accordance with monitored ocular parameters and the associated control functions. The stimulation signal may be adjusted directly, e.g., through the processor changing the way in which it produces the stimulation signal in accordance with the monitored ocular parameters and associated control functions, or indirectly, e.g., through the processor adjusting one or more functions of the image receiver that receives the images used to generate the stimulation signal, in accordance with the monitored ocular parameters and associated control functions. The monitored ocular parameters may provide a natural physical indication of how the visual percept should be varied.

One or more ocular parameters that are monitored may, for example, serve as a trigger for the associated control function to control the visual prosthesis apparatus. For example, when a particular ocular parameter is observed, or when a particular ocular parameter behaves in a certain way, the associated control function can be activated. Additionally or alternatively, one or more ocular parameters that are monitored may provide for changeable control of the visual prosthesis apparatus by the associated control function. For example, the way in which the control function controls the visual prosthesis apparatus may change depending on changes in the behaviour of the associated monitored ocular parameter.

By monitoring ocular parameters and controlling the apparatus accordingly, the visual prosthesis apparatus may more closely imitate the eye function of a healthy-sighted individual. Generally, for the purposes of this discussion, a healthy-sighted individual is a person whose eyes, including the lens, iris, pupil, and retina, and whose visual cortex, are fully functioning, and the person need not use a visual prosthesis to obtain a visual percept.

As one example, an ocular parameter that is monitored may be the size of at least one of the user's pupils, and an associated control function may be such as to maintain a particular brightness, or to change the brightness, of the visual percept experienced by the user dependent on the size or a change in size of one or both of the user's pupils. This may provide the visual prosthesis with an automatic light intensity or brightness compensation function. Since the iris controls the amount of light entering the eye by controlling the size of the pupil, if the pupil is deemed to have a relatively large size or is deemed to increase in size, the stimulation signal may be adjusted such that the visual percept is bright or is brightened and, if the pupil is deemed to have a relatively small size or is determined to reduce in size, the stimulation signal may be adjusted such that the visual percept is dark or darkened. This may mimic approximately the iris and pupil function of a healthy-sighted individual. Such an adjustment of the stimulation signal may be carried out directly by the processor, or it may be carried out by adjusting a sensitivity of the image receiver. For example, the size of an aperture or iris of the image receiver could be controlled in accordance with the estimated size or change in size of the user's pupil(s).

In the example described above, the brightness of the visual percept is generally increased in accordance with increases in pupil size and decreased in accordance with decreases in pupil size. This approach can rely on the changing size of the pupil providing an indication of the user's desire, e.g. subconsciously, to increase or decrease the brightness of the visual percept that they are experiencing. This approach may be particularly suited to users whose eyes have substantially no sensitivity to ambient light.

However, in some instances, a user of the apparatus may have sufficient sensitivity to ambient light via natural photosensitive structures in one or both eyes such that the size of their pupils normally varies in accordance with the ambient light level. In these instances, the pupil size would generally vary inversely with the ambient light level (i.e., pupil size would be smaller with higher illumination, and larger with lower illumination). Increased sensitivity to ambient light can affect the quality of the visual percept experienced by the user, particularly if the perceived brightness of the ambient light is relatively high in comparison to the part of the visual percept elicited by the stimulation device.

To compensate for problems associated with perception of ambient light, the apparatus may be configured to carry out automatic brightness or intensity compensation in accordance with the estimated apparent brightness of the ambient light determined from an estimation of pupil size. In general, in order to provide a more relevant or useful visual percept, the brightness of the part of the visual percept elicited by the stimulation device may be adjusted to ensure that it contrasts appropriately with the brightness of a part of the visual percept derived from the user's sensitivity to the ambient light.

Thus, if the pupil is determined to have a relatively small size or is deemed to reduce in size, the stimulation signal may be adjusted such that the part of the visual percept elicited by the stimulation device is relatively bright or is brightened, and if the pupil is determined to have a relatively large size or is deemed to increase in size, the stimulation signal may be adjusted such that the part of the visual percept elicited by the stimulation device is relatively dark or is darkened. This approach may be applied in cases where the user's pupil size has a greater dependency on ambient light levels than the perceived intensity of the part of the visual percept elicited by the stimulation signals. The approach may maintain a similar apparent or relative brightness of the part of the visual percept elicited by stimulation signals in the presence of varying levels of ambient illumination.

Adjustment of the brightness of the part of the visual percept elicited by the stimulation device may be carried out directly by the processor, e.g., by changing the amplitude of the stimulation signals, or it may be carried out by adjusting a sensitivity of the image receiver. For example, the size of an aperture or iris of the image receiver could be controlled in accordance with the estimated size or change in size of the user's pupil(s).

As another example, an ocular parameter that is monitored may be an open or closed state of at least one of the user's eyelids, and an associated control function may be such as to activate or deactivate (turn on or off) the visual percept experienced by the user dependent on the state or a change in state of the user's eyelids. This may provide for automatic visual prosthesis activation and deactivation based on the user's instinctive or conscious behaviour. Since one function of the eyelid in a healthy-sighted individual is to both permit and prevent light from entering the eye, causing and preventing a relevant visual percept being experienced by the user respectively, the stimulation signal may be maintained on or switched on when the eyelid is open or opened, and maintained off or switched off when the eyelid is closed. This may approximately mimic, in part, the eyelid function of a healthy-sighted individual. This may also provide the user with a means to disable the prosthesis relatively quickly and conveniently, if, for example, the stimulation provided by the prosthesis causes any pain or discomfort. Such an adjustment of the stimulation signal may be carried out directly by the processor or it may be carried out by adjusting the image receiver. For example, the processor may be configured to produce no stimulation signal when the eyelid is determined to be closed, regardless of the nature of the images received by the image receiver, or the aperture or iris of the image receiver could be opened or closed, or the image receiver turned on or off, in accordance with the open or closed state of at least one of the user's eyelids.

As another example, an ocular parameter that is monitored may be the direction of eye gaze of at least one of the user's eyes. An associated control function may be such as to select or scan over a portion of a visual percept of a visual scene, in accordance with the direction or a change in direction of the eye gaze. This may provide for automatic eye gaze adjustment and eye motion compensation. In a healthy-sighted individual, while maintaining a particular head position, the individual is capable of scanning a visual scene by changing the direction of eye gaze. Since only a portion of the images received by the image receiver, and thus only a portion of an available visual scene, may be used at any one time to create a visual percept for the user, there is the opportunity to select a portion of the images used to generate the stimulation signal such as to give the impression of scanning over or attending to or looking in one particular direction of a visual scene. In addition to or as an alternative to selecting a portion of the images used to generate the stimulation signal, the position of at least a part of the image receiver may be moved in accordance with the direction, or a change in direction, of the eye gaze. For example, the image receiver may include an image capture lens that is movable relative to another part of the image receiver and/or the entire image receiver may be moveable relative to e.g., the user's head, in accordance with the direction, or a change in direction, of the eye gaze.

Thus, with the visual prosthesis, a similar experience to that of a healthy-sighted individual may be created for the user by configuring the prosthesis such that, if the user places their eye gaze in any one direction (e.g., left, right, up, or down), or moves their eye gaze in that direction, the stimulation signal is directly or indirectly controlled such that the visual percept gives the user the impression of looking in that direction, or scanning in that direction, over a visual scene.

The arrangement may also allow for a user to achieve a visual percept of maintaining fixation on a particular feature of a visual scene, while moving their head. A healthy-sighted individual has a vestibulo-ocular reflex providing for a stabilization of images during head movement, such that an image can be maintained in the centre of the individual's field of view while moving their head. Thus, in relation to the visual prosthesis apparatus, if the image receiver is maintained in a substantially fixed position relative to the user's head, and the user moves their head, the ability to scan over what is a shifting visual scene can allow a particular portion of that visual scene to be maintained in the centre of the user's perceived field of view, mimicking approximately the vestibulo-ocular reflex of a healthy-sighted individual.

In one embodiment, the eye gaze adjustment may be used to compensate for fading of fixed images, known as Troxler's fading. Troxler's fading occurs, when a stimulus on the retina is kept stationary. After a short period of time, the perceived image resulting from the stationary stimulus appears to fade away and disappear. In a healthy-sighted individual, normal movements of the eye, or saccades, move the stimulus on the retina enough to avoid the adaptation of neurons that results in Troxler's fading. So that a user of the visual prosthesis apparatus may avoid the perception of fading in the visual percept, e.g., as a result of the image receiver being maintained in a fixed position for a period of time, a stimulation pattern in the stimulation signal may be moved, e.g., "jittered". By monitoring the direction of eye gaze as described above, small natural movements or saccades of the eye can be determined and the stimulation pattern moved accordingly. The movement can cause the user's brain to compensate for the Troxler's fading phenomenon, yet the brain may adapt to the movement such that it is not present in the visual percept.

In the non-limiting examples described above, the control functions associated with the monitored ocular parameters are substantially consistent with the natural eye function of a healthy-sighted individual. However, additionally or alternatively, control functions associated with the monitored ocular parameters may not be consistent with natural eye function, and may provide instead for enhanced user control.

For example, monitored ocular parameters may be associated with one or more of the control functions set forth in the following list or otherwise:

fine tuning of the brightness or intensity of the visual percept, adjusting of the contrast of the visual percept, adjusting of a degree of zoom such as to give the user the impression through the visual percept of focussing in on, or drawing away from, a particular portion of a visual scene;

switching between a visual percept of a positive or a negative image activating or deactivating functionality of the visual prosthesis such as the ability of the visual prosthesis to perform the automatic light intensity or brightness compensation, the visual prosthesis activation based on eyelid state detection and/or the eye direction adjustment or otherwise;

changing a processing mode of the processor, such as a face detection mode, a navigation mode or an edge detection mode or otherwise; and activating or deactivating one or more feedback devices, such as speakers or tactile devices.

The monitored ocular parameters associated with the control functions may be one or more of the parameters set forth in the following list or otherwise:

a sequence of blinks, e.g. a double blink;

a sequence of winks, e.g. right or left eye single winks or double winks, analogous to right and left single and double computer mouse button clicks;

the maintaining of eye gaze in a predetermined position for a predetermined period of time, e.g. maintaining eye gaze as far left or right as possible for at least 4 seconds, etc.;

the squinting and/or crossing of the eyes, e.g. for a predetermined period of time, e.g., crossing the eyes for at least 5 seconds; and the raising of at least one eyebrow.

A number of the control functions associated with the enhanced user control may be carried out by adjusting the stimulation signal directly, e.g., through the processor changing the way in which it produces the stimulation signal in accordance with the monitored ocular parameters and associated control functions, or indirectly, e.g., through the processor adjusting one or more functions of the image receiver that receives the images used to generate the stimulation signal in accordance with the monitored ocular parameters and associated control functions. For example, regarding the zoom control function, since only a portion of the images received by the image receiver, and thus only a portion of an available visual scene, may be used at any one time to create a visual percept for the user, there is the opportunity to directly adjust the stimulation signal by selecting a smaller or larger portion of the images used to generate the stimulation signal such as to give the visual percept of zooming in on or zooming out of a visual scene. In addition to or as an alternative to selecting a smaller or larger portion of the images used to generate the stimulation signal, a zoom function integral to the image receiver may be controlled to change the magnification of the received images.

The control functions may be initiated upon monitoring any one or more of the ocular parameters on their own, or in combination with a separate action, e.g. in combination with a manual input or an acoustic input to the visual prosthesis apparatus. A manual input may comprise the user pressing a button, including depressing a push button, rotating a knob, or moving a slider, for example. An acoustic input may comprise the user uttering a word or producing a sound that is picked up by a microphone. By requiring a manual or acoustic input to be present during the monitoring of a particular ocular parameter, unwanted initiation of a control function may be prevented.

The image receiver can produce an image signal in accordance with the plurality of images. The image receiver may be a video camera and the image signal may be a video signal, for example. The image receiver may be worn on the user's head, e.g. through mounting of the image receiver on glasses frames or a head band or a hat.

The processor can receive the image signal and produce the stimulation signal at least partially in accordance with the received image signal.

The stimulation device may be implanted in or on the user's eye or in or on the visual cortex of the user's brain. The stimulation device can include a plurality of electrodes configured to deliver current to different portions of the user's eye or brain, such as retinal nerve cells, to stimulate the user's visual neurons. The electrodes can be individually addressed, through a switch matrix or otherwise.

As indicated above, the monitored eye regions may include both the eyeball and the eyelid. However, in some embodiments, only the eyeball may be monitored, e.g. if eyelid state monitoring is not to be performed, or only the eyelid may be monitored, e.g. if pupil size or eye gaze monitoring is not to be performed. In addition or as an alternative to the eyeball and/or eyelid monitoring, the monitored eye regions may extend further and include elements such as the eyebrows.

The eye monitoring device may produce an eye monitoring signal based on the monitoring of the ocular parameters and the processor may be configured to receive the eye monitoring signal. The processor may be configured to adjust the stimulation signal or other features of the apparatus in accordance with the received eye monitoring signal and the control functions. The eye monitoring device may be worn on the user's head, e.g. through mounting of the eye monitoring device on glasses frames or a head band or a hat. The eye monitoring device may be integrated into the same device or unit as the image receiver or otherwise.

The eye monitoring device may be an eye tracker that is already available for use in marketing research, usability testing, ophthalmology and other industries, for example, and which can monitor pupil size, eyelid state, blink detection and/or direction of eye gaze or otherwise. In this regard, the eye tracker may be a video-based system, which uses a camera that focuses on one or both eye regions of the user, and which may use infrared and/or near infrared to create a corneal reflection. However, the eye monitoring device may employ alternative or additional approaches to monitoring. For example, to determine eye gaze direction, an attachment may be applied to the eye, such as a mirror or magnetic field sensor, with the movement of the attachment being monitored. In another example, an electromagnetic coupling between one or more pairs of coils that transmit power and/or data through the sclera into and/or out of the eye may provide information about eye gaze direction. As another alternative, electrodes may be used to measure changes in electrical potentials at the eye region associated with eye movement. As yet another alternative, a device such as an accelerometer may be implanted in the eye, which can be used to estimate the eye gaze direction or change in direction.

In one embodiment, at least two different ocular parameters may be monitored. For example, the eye monitoring device may be configured to measure at least pupil size and eyelid state, or at least eyelid state and eye gaze, or at least pupil size, eyelid state and eye gaze. In another embodiment, only one ocular parameter may be measured. For example, the eye monitoring device may be configured to monitor pupil size only, eyelid state only, or eye gaze only.

In a second aspect, there is provided a processor for a visual prosthesis apparatus, the processor comprising:

an image signal receiving module configured to receive an image signal from an image receiver, the image signal generated in accordance with a sequence of images received by the image receiver;

a stimulation module configured to produce a stimulation signal at least partially in accordance with the image signal, the stimulation signal being for transmission to a stimulation device, the stimulation device configured to receive the stimulation signal and stimulate visual neurons of a user in accordance with the stimulation signal to provide the user with a visual percept;

an eye monitoring module configured to receive an eye monitoring signal from an eye monitoring device such as to monitor one or more ocular parameters of at least one eye region; and a control module configured to control the visual prosthesis apparatus in accordance with one or more control functions associated with one or more of the monitored ocular parameters.

The processor of the second aspect may have any one or more of the processing features described with respect to the processor of the first aspect. The processor of the second aspect may be used as the processor in the visual prosthesis apparatus of the first aspect.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF THE DRAWINGS

By way of example only, embodiments are now described with reference to the accompanying drawings, in which:

FIGS. 4a to 5b illustrate exemplary eye gaze functionality of a visual prosthesis apparatus.

DETAILED DESCRIPTION

Figure 1A:
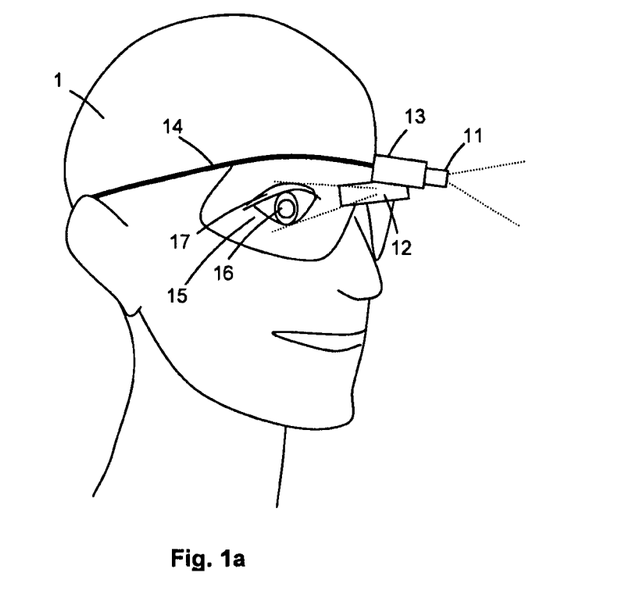
FIGS. 1a and 1b show an embodiment of a visual prosthesis apparatus.
Figure 1B:
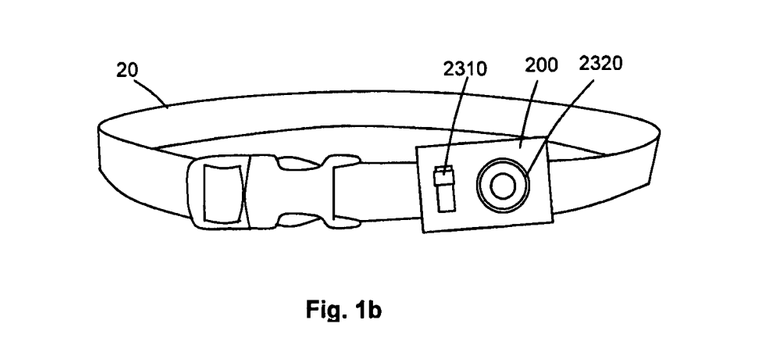

Visual prosthesis apparatus according to one embodiment is shown in FIGS. 1a and 1b. Schematic illustration of the components of the visual prosthesis is also provided in FIGS. 2a and 2b.

The visual prosthesis apparatus comprises a video camera 11 and an eye monitoring device 12. The video camera 11 and eye monitoring device 12 are integrated into a single unit 13 in this embodiment, which unit 13 is mounted on frames of a pair of glasses 14, supported on the head of the user 1.

The video camera 11 is forward facing and is configured to capture images in front of the user 1 and transmit a corresponding video signal 211 to a video signal receiver 21 of a processor 2. In this embodiment, the processor 2 is located in a housing 200 on a belt 20, to be worn around the waist of the user 1.

The eye monitoring device 12 is rearward facing and is configured to capture images of at least one eye region 15 of the user 1, including an eye 16 and an eyelid 17, and transmit a corresponding eye monitoring signal 221 to a monitoring signal receiver 22 of the processor 2. The eye monitoring device 12 may, at least in part, function as a second video camera, with the eye monitoring signal 221 being a second video signal.

Figure 3A:
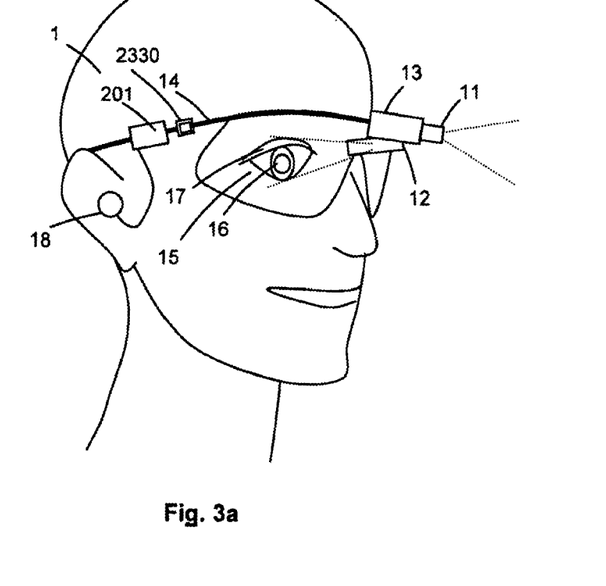
FIGS. 3a and 3b show two further embodiments of a visual prosthesis apparatus.
Figure 3B:
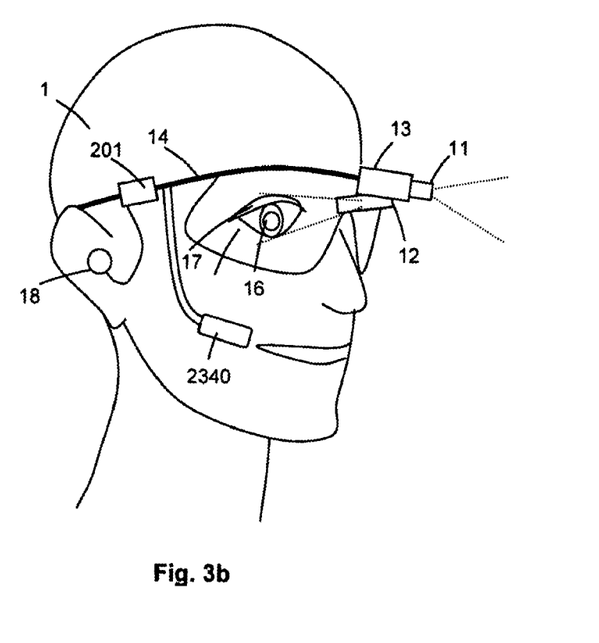

Although the processor 2 in this embodiment is located in the housing 200 on the belt 20, it may be located elsewhere. For example, the processor 2 can be located in a housing 201 on the lens frames, as illustrated in FIGS. 3a and 3b. Alternatively, it can be integrated into the unit 13, or otherwise. Communication between the video camera 11, eye monitoring device 12 and the processor 2 can be via wires, or through wireless communication.

Figure 2A:
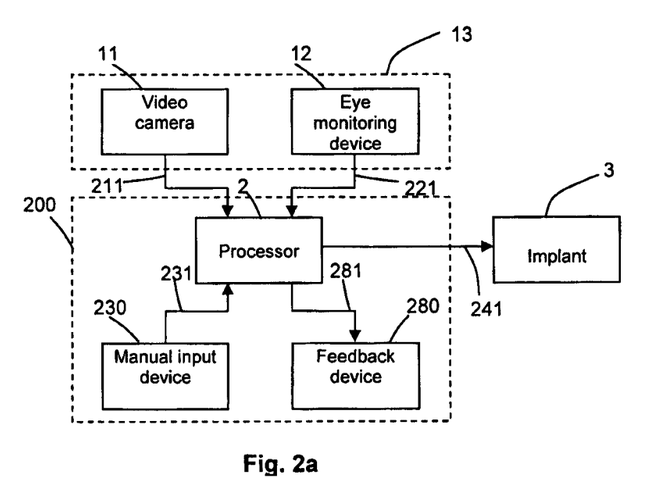
FIGS. 2a and 2b provide schematic illustrations of components of the visual prosthesis apparatus of FIGS. 1a and 1b.
Figure 2B:
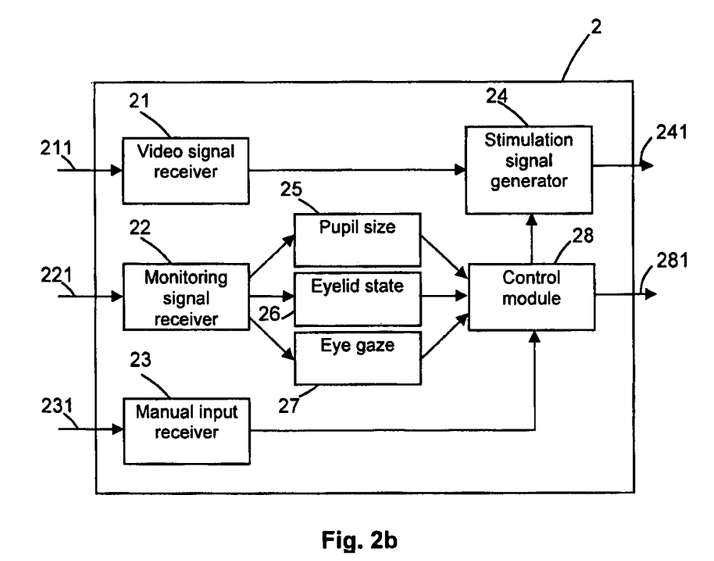

The processor 2 includes a stimulation signal generator 24 configured to generate a stimulation signal 241 based at least in part on a portion of the video signal images. The stimulation signal 241 is delivered to an implantable component 3 of the visual prosthesis apparatus. The implantable component 3 in this embodiment is located on or embedded in an eye of the user, which can be the eye 16 monitored by the eye monitoring device or the other eye of the user. The implantable component 3 includes an array of electrodes that, based at least in part on the stimulation signal, are configured to deliver current to stimulate visual neurons of the user, providing the user with a visual percept. In alternative embodiments, electrodes of the implantable component may be placed directly on the visual cortex of the user's brain or otherwise.

Generally, the processor 2 is configured to stimulate, via the stimulation signal 241 and electrodes of the implantable component 3, the visual neurons of the user in a manner that provides the user with a visual percept of at least a portion of the video images received by the video camera 11. Accordingly, vision of a healthy-sighted individual may be approximately simulated. However, to more closely simulate vision of a healthy-sighted individual, and to provide enhanced user operation of the visual prosthesis apparatus, the visual prosthesis apparatus is also configured to adapt its operation in accordance with the status or behaviour of ocular parameters of the monitored eye region 15.

In this embodiment, the following ocular parameters at the eye region 15 are monitored:
  size of the pupil of the eye 16;
  open or closed state of the eyelid 17; and
  direction of eye gaze of the eye 16.

Monitoring of the ocular parameters is achieved through the processor 2 analysing one or more successive video images captured by the eye monitoring device. A plurality of monitoring modules are used to perform the analysis, including a pupil size module 25, an eyelid state module 26 and an eye gaze module 27. The images are provided in pixelated form, and the monitoring modules are configured to determine ocular parameters, statuses, and behaviours using image processing techniques.

In particular, the pupil size module 25 is configured to estimate the diameter of the pupil, which is indicative of the pupil size. The eyelid state module 26 is configured to determine the presence or absence of features of the eye such as the iris or pupil, which is indicative of whether the eyelid is open (features are present) or closed (features are absent). The eye gaze module 27 is configured to estimate the location of the centre of the eye; e.g., the centre of the pupil and its location in the image, which is indicative of the direction of gaze of the eye.

A variety of different approaches can be used to monitor the ocular parameters, however, in conjunction with or as an alternative to those described above. For example, the pupil size module 25 may estimate the radius or area of the pupil instead of the diameter. As another example, the eyelid state module 26 may estimate the location of a bottom portion of the eyelid. As yet another example, the eye gaze module 27 may estimate a degree of rotation of the eye, or a velocity of movement of the eye. If velocity is determined, the direction of eye gaze may be extrapolated from a reduced number of images, for example.

The processor 2 comprises a control module 28 that is coupled to the stimulation signal generator 24 and configured to alter the stimulation signal 241 based on ocular parameter information determined by the monitoring modules 25, 26, 27. Particularly, the control module 28 is configured to carry out different control functions associated with different ocular parameter statuses and/or behaviours that have been determined by the monitoring modules 25, 26, 27, such as to alter the stimulation signal.

In more detail, in this embodiment, the control module 28 is configured to carry out automatic brightness or intensity compensation by varying an intensity of the stimulation signal 241 dependent on the pupil size estimated by the pupil size module 25. The arrangement is such that the brightness of the visual percept experienced by the user is at least partially dependent on the estimated size of the monitored pupil. Since the iris normally controls the amount of light entering the eye by controlling the size of the pupil, if the pupil is determined to have a relatively large size or is deemed to increase in size, the stimulation signal is adjusted by the control module 28 such that the visual percept is relatively bright or is brightened. On the contrary, if the pupil is determined to have a relatively small size or is deemed to reduce in size, the stimulation signal is adjusted such that the visual percept is relatively dark or is darkened. The intensity of the stimulation signal is adjusted directly by the control module 28 in this embodiment. However, in alternative embodiments, the size of an image receiving aperture or iris of the video camera may be adjusted by the processor dependent on the estimated size of the pupil, to change the brightness or intensity of the received images used to generate the stimulation signal.

In alternative embodiments, however, if the pupil is determined to have a relatively large size or is deemed to increase in size, the stimulation signal can be adjusted by the control module such that the visual percept is relatively dark or is darkened. On the contrary, if the pupil is determined to have a relatively small size or is deemed to reduce in size, the stimulation signal is adjusted such that the visual percept is relatively bright or is brightened. This approach may be applied in cases where the user is sensitive to ambient light and the user's pupil size has a greater dependency on ambient light levels than the perceived intensity of the part of the visual percept elicited by the stimulation signals. The approach may allow the brightness of the part of the visual percept elicited by the stimulation device to be adjusted so that it contrasts more appropriately with the brightness of a part of the visual percept derived from the user's sensitivity to the ambient light.

The control module 28 is also configured to turn on or off the stimulation signal 241 dependent on the eyelid state determined by the eyelid state module 26. The arrangement is such that the visual percept is activated or deactivated (turned on or off) in accordance with the open or closed state, respectively, of the user's eyelid 17. The stimulation signal 241 is turned on and off directly by the control module 28 in this embodiment. However, in alternative embodiments, the processor may be configured to cause an aperture or iris of the video camera to be opened or closed, or the video camera to be turned on or off, in accordance with the open or closed stated, respectively, of the user's eyelid.

The control module 28 is also configured to modify the stimulation signal 241 such as to provide a visual percept of selecting or scanning over a portion of a visual scene in accordance with the direction of eye gaze determined by the eye gaze module 27. Thus, if, for example, the user's eye gaze is determined to be in a left of centre direction, the control module 28 is configured to adjust the stimulation signal such that the signal is based on a left of centre portion of one or more of the video signal images. Similarly, if, for example, the user's eye gaze is determined to be in a bottom of centre direction, the control module is configured to adjust the stimulation signal such that the stimulation signal is based on a bottom of centre portion of one or more of the video signal images. To facilitate this operation, in this embodiment, the video camera 11 is provided with a relatively wide field of view, and therefore only a section of each of the video signal images it receives need be used to generate the stimulation signal. Exemplary operation of this eye gaze functionality is described in the following examples with reference to FIGS. 4a and 4b and FIGS. 5a and 5b.

Figure 4A:
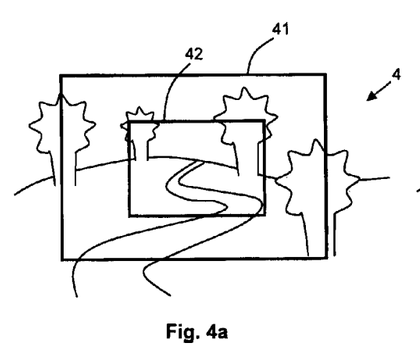
Figure 4B:
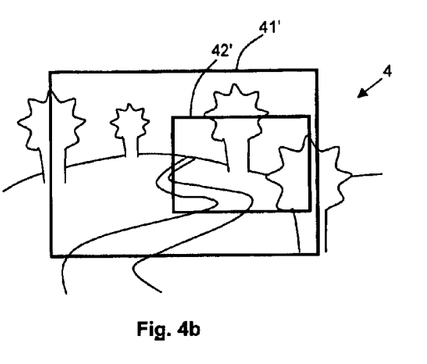

Referring to FIG. 4a, a portion of a visual scene 4, located in front of the user, captured as first video image at a first point in time, is represented by rectangle 41. In FIG. 4b, a portion of the visual scene 4, captured as a second video image at a second point in time, is represented by rectangle 41'. Between the capture of the first and second video images 41, 41', the user has maintained his/her head, and thus the video camera, in substantially the same forward-facing position, and accordingly the positioning of the first and second video images 41, 41' relative to the visual scene 4 is substantially identical.

At the first point in time, the user's direction of eye gaze is determined by the eye gaze module 27 to be in a substantially central direction. Accordingly, the control module 28 is configured such that the stimulation signal, at substantially the first point in time, is based on a central portion 42 of the first video image 41. At the second point in time the user's direction of eye gaze determined by eye gaze module 27 is in a right of centre direction. Accordingly, the control module 28 is configured such that the stimulation signal, at substantially the second point in time, is generated based on a right of centre portion 42' of the second video image 41'. Thus, between the stimulation based on the first and second video images, the visual percept experienced by the user gives the user the impression of scanning to the right of a visual scene.

Figure 5A:
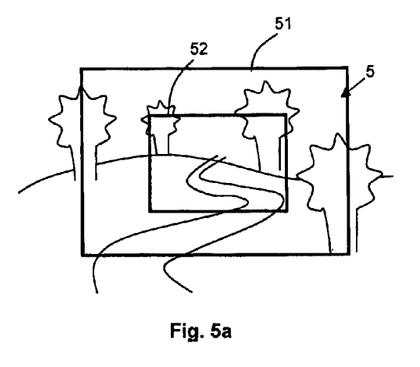
Figure 5B:
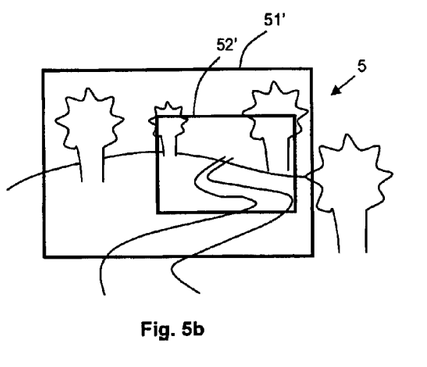

In FIG. 5a, a portion of a visual scene 5, located in front of the user, captured as third video image at a third point in time, is represented by rectangle 51. In FIG. 5b, a portion of the visual scene 5, captured as a fourth video image at a fourth point in time, is represented by rectangle 51'. Between the capture of the third and fourth video images 51, 51', the user has moved his/her head, and thus the video camera, towards the left of the visual scene 5. Thus the fourth video image 51' corresponds to a portion of the visual scene 5 located more to the left of the visual scene than the third video image 51.

At the third point in time, the user's direction of eye gaze is determined by the eye gaze module 27 to be in a substantially central direction. Accordingly, the control module 24 is configured such that the stimulation signal, at substantially the third point in time, is based on a central portion 52 of the third video image 51. At the fourth point in time the user's direction of eye gaze determined by eye gaze module 27 is in a right of centre direction. Accordingly, the control module 28 is configured such that the stimulation signal, at substantially the second point in time, is generated based on a right of centre portion 42' of the second video image 41'. In this example, the movement of the eye gaze to the right of centre approximately compensates for the opposing movement of the head and video camera to the left of centre. Thus, between the stimulation based on the third and fourth video images 51, 51', the visual percept experienced by the user gives the user the impression of maintaining fixation on the same portion of a moving visual scene. This functionality is akin to the vestibulo-ocular reflex, providing for a stabilization of images during head movement, experienced by healthy-sighted individuals.

The approach described above provides for direct adjustment of the stimulation signal by the control module 28, in accordance with the direction, or a change in direction, of the eye gaze. However, in alternative embodiments, the video camera may include an image capture lens that is movable relative to another part of the video camera, and/or the entire video camera may be moveable relative to e.g., the user's head, and the processor may be configured to control the movement of the lens or entire video camera in accordance with the direction, or a change in direction, of the eye gaze.

As indicated, the processor 2 comprises a number of processing modules. The processor also includes one or more storage elements, for storing data related to the monitored ocular parameters and control function instructions, etc. The modules and storage elements can be implemented using one or more processing devices and one or more data storage units that can form the processor, and which modules and/or storage devices may be at one location or distributed across multiple locations and interconnected by one or more communication links.

The processing modules can be implemented by a computer program or program code comprising program instructions. The computer program instructions can include source code, object code, machine code or any other stored data that is operable to cause the processor to perform the steps described. The computer program can be written in any form of programming language, including compiled or interpreted languages and can be deployed in any form, including as a stand-alone program or as a module, component, subroutine or other unit suitable for use in a computing environment. The data storage device(s) may include suitable computer readable media such as volatile (e.g. RAM) and/or non-volatile (e.g. ROM, disk) memory or otherwise.

The operation of the processor 2 in the embodiments described above is such as to provide control of the stimulation signal, based on the monitored ocular parameters, that is substantially consistent with the natural eye function of a healthy-sighted individual. However, the processor is also configured to provide enhanced user control, through application of additional control functions to those described above. In general, these additional control functions may be considered to provide enhanced user control on the basis that there is no equivalent function in relation to the eyesight of a healthy-sighted individual.

First, additional control functions are associated with the eyelid state monitoring. In particular, if the eyelid state module 26 determines that the user performs a double blink within a predetermined time period of e.g. 0.5 seconds, the control module 28 is configured to adjust the stimulation signal such that it is generated based on a smaller portion of a visual scene, giving the user the impression of zooming in on the visual scene. On the other hand, if the eyelid state module 26 determines that the user performs a triple blink within the predetermined period, the control module 28 is configured to adjust the stimulation signal such that it is generated based on a larger portion of the visual scene, giving the user the impression of zooming out of the visual scene.

Second, additional control functions are associated with the eye gaze monitoring. If the eye gaze module 27 determines that the user holds their eyes towards the top of centre for a predetermined period of e.g., 2 seconds, the control module 28 is configured to adjust the stimulation signal such that the visual percept switches between a positive and a negative image. On the other hand, if the eyelid gaze module 27 determines that the user holds their eyes towards the bottom of centre for the predetermined period, the control module 28 is configured to adjust the stimulation signal such that the perceived contrast of the visual percept is altered.

When carrying out the enhanced user control described above, the user in this embodiment must simultaneously make a manual input to the processor 2 using one or more manual input devices 230. In particular, in the embodiments described with respect to FIGS. 1a to 2b, the user must press a button acting as a manual input device 230, which is connected to the processor 2, and which causes a manual input signal 231 to be transmitted to a manual input receiver 23 of the processor 2. This manual input ensures that the enhanced user control is not activated unintentionally, e.g. during a reflex double blink, or while the user is holding their eye gaze in a specific position for the predetermined period of time to observe a particular portion of the visual scene, etc. In the embodiment discussed in relation to FIGS. 1a to 2b, the button is a slide button 2310 located on the belt 20, on the outer wall of the housing 200 that accommodates the processor 2. In alternative embodiments, a different type of button may be used to provide a manual input, or an acoustic input may be used in place of a manual input.

For example, in the embodiment illustrated in FIG. 3a, the button is a push button 2330 located on the lens frames 14. Further, in the embodiment illustrated in FIG. 3b, a microphone 2340, acting as an acoustic input device, is used in place of a button. The microphone 2340 is connected to the processor 2 and, in combination with the processor 2, is configured to monitor for voice commands from the user. For example, the user may utter the word "adjust" at the same time, or within a few seconds, e.g., 2 seconds, of carrying out a control action using their eye.

One or more feedback devices 280, are connected to the processor 2 to alert the user or confirm to the user that a specific control function has been initiated and/or that a manual input has been made. In the embodiment discussed in relation to FIG. 1a, a vibration device and a loudspeaker 2320 provide feedback devices 280 and are located in the housing 200 on the belt 20 to provide feedback following receipt of a feedback signal 281 generated by the processor. In the embodiments illustrated by FIGS. 3a and 3b, an earphone 18 is connected to the processor 2 to provide feedback. The feedback provided by the feedback devices 280 may, for example, be in the form of a voice message to confirm the state of the processor such as "battery low", "maximum zoom", "minimum brightness", "program 1", "face detection mode", etc.

In alternative embodiments, a variety of other control functions can be initiated based on the monitoring of different ocular parameters, such as: fine tuning of the brightness of the visual percept; activating or deactivating functionality of the visual prosthesis (e.g.: the ability of the visual prosthesis to perform the automatic brightness compensation, the visual prosthesis activation based on eyelid state detection and/or the eye direction adjustment or otherwise); changing a processing mode of the processor (e.g. a face detection mode, a navigation mode or an edge detection mode); and/or activating or deactivating one or more of the feedback devices.

Further, in alternative embodiments, control functions can be initiated based on the monitoring of a variety of different ocular parameters. For example, winking the right or left eye, squinting and/or crossing the eyes for a predetermined period of time, or raising of an eyebrow, may be monitored and used as one or more triggers for initiating control functions.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A visual prosthesis apparatus comprising:
   an image receiver configured to receive a sequence of images;
   a processor coupled to the image receiver, the processor configured to produce a stimulation signal at least partially in accordance with the received images;
   a stimulation device coupled to the processor, the stimulation device configured to receive the stimulation signal and stimulate visual neurons of a user in accordance with the stimulation signal to provide the user with a visual percept; and
   an eye monitoring device coupled to the processor such as to monitor one or more ocular parameters of at least one eye region of the user;
   wherein one or more control functions are associated with the monitored ocular parameters;
   wherein the processor is configured to control the visual prosthesis apparatus in accordance with the monitored ocular parameters and the associated control functions; and
   wherein the control of the visual prosthesis apparatus by the processor comprises automatically adjusting the image receiver in accordance with one or more of the monitored ocular parameters and the associated control functions to adjust the stimulation signal indirectly.

2. The apparatus of claim 1, wherein one of the ocular parameters that is monitored is the size of at least one of the user's pupils.

3. The apparatus of claim 2, wherein one of the control functions associated with the monitoring of the size of at least one of the user's pupils is an automatic brightness control function such as to maintain a brightness or intensity, or change the brightness or intensity, of the visual percept in accordance with the size of at least one of the user's pupils.

4. The apparatus of claim 3, wherein the brightness control function is configured to maintain or adjust an amplitude of the stimulation signal in accordance with the size of at least one of the user's pupils.

5. The apparatus of claim 3, wherein automatically adjusting the image receiver comprises adjusting the size of an aperture of the image receiver in accordance with the monitored size of at least one of the user's pupils.

6. The apparatus of claim 1, wherein one of the ocular parameters that is monitored is an open or closed state of at least one of the user's eyelids.

7. The apparatus of claim 6, wherein one of the control functions associated with the monitoring of the open or closed state of at least one of the user's eyelids is an on/off control function such as to substantially activate or maintain active, or substantially deactivate or maintain inactive, the visual percept experienced by the user in accordance with the open or closed state of at least one of the user's eyelids.

8. The apparatus of claim 1, wherein one of the ocular parameters that is monitored is a direction of eye gaze of at least one of the user's eyes.

9. The apparatus of claim 8, wherein one of the control functions associated with the monitoring of direction of eye gaze is a selecting/scanning control function configured to provide for selection or scanning over a visual percept of a scene in accordance with the monitored direction of eye gaze.

10. The apparatus of claim 9, wherein at least a part of the image receiver is configured to be moved relative to the user, and wherein automatically adjusting the image receiver comprises moving at least a part of the image receiver being in accordance with the monitored direction of eye gaze.

11. The apparatus of claim 9, wherein the selecting/scanning control function is configured such as to provide the visual prosthesis apparatus with an image stabilization function.

12. The apparatus of claim 9, wherein the selecting/scanning control function is configured such as to provide the visual prosthesis apparatus with an anti-fading function.

13. The apparatus of claim 1, wherein one of the control functions is configured such as to adjust the intensity or brightness of the visual percept in accordance with one of the monitored ocular parameters that is not the size of a pupil of the user's eyes.

14. The apparatus of claim 1, wherein one of the control functions is configured such as to provide the user with a visual percept of zooming in or zooming out of a visual scene, in accordance with one of the monitored ocular parameters.

15. The apparatus of claim 14, wherein the image receiver has an integral zoom and automatically adjusting the image receiver comprises using the integral zoom to zoom in or zoom out in accordance with one of the monitored ocular parameters.

16. The apparatus of claim 1, wherein one of the control functions is configured such as to switch between providing the user with a visual percept of a positive and a negative image, in accordance with one of the monitored ocular parameters.

17. The apparatus of claim 1, wherein one of the control functions is configured such as to activate or deactivate one or more other of the control functions of the visual prosthesis apparatus, in accordance with one of the monitored ocular parameters.

18. The apparatus of claim 1, wherein one of the control functions is configured to change or activate or deactivate a processing mode of the processor, in accordance with one of the monitored ocular parameters.

19. The apparatus of claim 1, wherein the apparatus comprises one or more feedback devices configured to provide feedback to the user regarding activation of one or more of the control functions.

20. The apparatus of claim 19, wherein one of the control functions is configured to activate or deactivate one or more of the feedback devices, in accordance with one of the monitored ocular parameters.

21. The apparatus of claim 1 wherein one or more of the monitored ocular parameters are selected from the following list of ocular parameters:
- blinking of both of the user's eyelids;
- winking of one of the user's eyelids;
- maintaining of eye gaze of at least one of the user's eyes in a predetermined direction for a predetermined period of time;
- squinting and/or crossing of the user's eyes; and
- raising of at least one of the user's eyebrows.

22. The apparatus of claim 1, wherein one or more of the control functions are configured to be carried out only after or during the provision of a manual input and/or acoustic input to the visual prosthesis.

23. The apparatus of claim 1, wherein one or more of the monitored ocular parameters is blinking of both of the user's eyelids or winking of one of the user's eyelids.

24. The apparatus of claim 1, wherein one or more of the monitored ocular parameters is maintaining of eye gaze of at least one of the user's eyes in a predetermined direction for a predetermined period of time.

25. The apparatus of claim 1, wherein one or more of the monitored ocular parameters is squinting and/or crossing of the user's eyes.

26. The apparatus of claim 1, wherein one or more of the monitored ocular parameters is raising of at least one of the user's eyebrows.

27. The apparatus of claim 6, wherein automatically adjusting the image receiver comprises turning on or turning off the image receiver in accordance with the monitored open or closed state of the at least one of the user's eyelids.

* * * * *